United States Patent [19]
Moslehi

[11] Patent Number: 5,474,381
[45] Date of Patent: Dec. 12, 1995

[54] METHOD FOR REAL-TIME SEMICONDUCTOR WAFER TEMPERATURE MEASUREMENT BASED ON A SURFACE ROUGHNESS CHARACTERISTIC OF THE WAFER

[75] Inventor: Mehrdad M. Moslehi, Dallas, Tex.

[73] Assignee: Texas Instruments Incorporated, Dallas, Tex.

[21] Appl. No.: 160,595

[22] Filed: Nov. 30, 1993

[51] Int. Cl.$^6$ .................................................. G01K 11/00
[52] U.S. Cl. ........................................... 374/161; 374/120
[58] Field of Search ..................................... 374/161, 120, 374/45, 4, 7; 356/371, 447

[56] References Cited

U.S. PATENT DOCUMENTS

| | | | |
|---|---|---|---|
| 4,823,348 | 4/1989 | Hercher | 372/32 |
| 4,969,748 | 11/1990 | Crowley et al. | 374/1 |
| 4,984,902 | 1/1991 | Crowley et al. | 374/1 |
| 5,206,710 | 4/1993 | Geiler et al. | 356/447 |
| 5,263,776 | 11/1993 | Abraham et al. | 374/120 |
| 5,293,215 | 3/1994 | Pfendler et al. | 356/360 |
| 5,298,970 | 3/1994 | Takamatsu et al. | 356/360 |
| 5,350,899 | 9/1994 | Ishikawa et al. | 374/120 |
| 5,352,038 | 10/1994 | Schmidt et al. | 374/161 |

FOREIGN PATENT DOCUMENTS

| | | | |
|---|---|---|---|
| 0014021 | 1/1983 | Japan | 374/161 |
| 0160028 | 7/1986 | Japan | 374/120 |
| 0002111 | 1/1987 | Japan | 356/371 |
| 0305228 | 12/1988 | Japan | 374/120 |
| 0142305 | 6/1991 | Japan | 356/371 |
| 403165202 | 7/1991 | Japan | 356/371 |
| 404116416 | 4/1992 | Japan | 356/447 |
| 405264249 | 10/1993 | Japan | 356/371 |
| 1004755 | 3/1983 | U.S.S.R. | 374/7 |

*Primary Examiner*—Diego F. F. Gutierrez
*Attorney, Agent, or Firm*—Carlton H. Hoel; W. James Brady; Richard L. Donaldson

[57] ABSTRACT

A sensor (100) for measuring semiconductor wafer (10) temperature in semiconductor processing equipment (30), comprising a first laser (104) to provide a first laser beam at a first wavelength and a second laser (106) to provide a second laser beam at a second wavelength. The sensor also includes laser driver (108) and oscillator (110) to modulate the wavelength of the first and second laser beams as the laser beams are directed to and reflected from the wafer (10), and detector module (130) to measure the change in specular reflectance of the wafer (10) resulting from the modulation of the wavelength of the first and second laser beams. The sensor system also includes signal processing circuitry (138) to determine rms surface roughness of wafer (10) at a known reference temperature from the change in reflectance of wafer (10) resulting from modulation of the wavelengths of the first and second laser beams, and to determine the temperature of wafer (10) from the change in specular reflectance of wafer (10) resulting from modulation of the wavelengths of the first and second laser beams while wafer (10) is at an unknown temperature and the surface roughness of the wafer at the known temperature.

4 Claims, 5 Drawing Sheets

METHOD FOR REAL-TIME SEMICONDUCTOR WAFER TEMPERATURE MEASUREMENT BASED ON A SURFACE ROUGHNESS CHARACTERISTIC OF THE WAFER

The U.S. government has a paid-up license in this invention and the right in limited circumstances to require the patent owner to license others on reasonable terms as provided by the terms of the contract between assignee and the United States Air Force under the program name MMST.

TECHNICAL FIELD OF THE INVENTION

The present invention relates in general to real-time measurement of semiconductor wafer physical characteristics, and more particularly to a method and apparatus for non-invasive semiconductor wafer temperature measurements based on surface roughness induced scattering of laser beams.

BACKGROUND OF THE INVENTION

Integrated circuit chip manufacturers fabricate semiconductor devices by different combinations of fabrication processes. Wafer temperature is an important parameter for many of these processes. More specifically, precise measurement and control of wafer temperature and its uniformity are required in order to minimize deviations from the target process parameters and increase device fabrication yield. Thermal fabrication processes, such as thermal anneals, oxidation, and chemical vapor deposition (CVD) are examples of processes where wafer temperature is an important process parameter. Currently, thermocouples are used to measure wafer temperature during plasma etch operations such as reactive ion etch (RIE). Additionally, some chemical vapor deposition processes, such as plasma-enhanced chemical vapor deposition (PECVD) employ thermocouples for temperature measurement.

Thermocouples for measuring temperature in semiconductor fabrication equipment have substantial disadvantages. For instance, thermocouples can be disturbed by the RF and electromagnetic fields (e.g., 13.56 MHz RF and 2.45 GHz microwave) used to generate plasma during plasma etch processing. Thermocouples are also invasive in that they must be placed very near the location where the temperature is being measured. In some applications the thermocouples may require actual contact with the wafer surface for accurate temperature sensing, thereby causing disturbance of the wafer temperature and also possible wafer contamination. Furthermore, most thermocouples suffer from measurement error and slow response time problems.

Pyrometry providing for non-contact operation can also be used to measure wafer temperature in some thermal processing applications such as rapid thermal processing (RTP). Computational pyrometry sensors, however, have several disadvantages. For example, for accurate pyrometry-based temperature measurements, an accurate knowledge of the spectral emissivity of the wafer at the pyrometry measurement wavelength band is required. It is known that spectral emissivity can vary with various parameters, such as wafer temperature, wafer resistivity, material layers, and their thickness, and process chamber geometry and materials, making pyrometry sensors relatively inaccurate due to emissivity variations and other noise sources. In general, conventional pyrometry techniques can suffer from measurement inaccuracies and repeatability errors as high as ±100° C. or more. Moreover, pyrometry techniques require frequent cross-calibrations using thermocouples introducing the problems associated with thermocouples noted previously.

SUMMARY OF THE INVENTION

Therefore, a need has arisen for a method and apparatus for accurate and repeatable measurement of the temperature of a semiconductor wafer during device fabrication processing.

A need exists for a wafer temperature sensor which is not affected or disturbed by RF and electromagnetic fields which may be present during wafer processing.

A need further exists for a wafer temperature sensor which is non-invasive to the semiconductor wafer process.

A further need exists for a wafer temperature sensor which is not susceptible to error and slow response.

A need further exists for a wafer temperature sensor which does not depend on knowledge of spectral emissivity of the wafer to determine its temperature.

Yet a further need exists for a wafer temperature sensor which does not require cross-calibrations with additional temperature sensors.

In accordance with the present invention, a method, system and apparatus are provided which substantially eliminate or reduce disadvantages and problems associated with prior wafer temperature measuring sensors.

The present invention provides a sensor for real-time temperature measurements in processing equipment. The sensor includes an optical energy source for providing optical energy with a known spectral characteristic. The sensor also includes an optical system for transmitting at least a portion of the optical energy towards a workpiece and for receiving at least a portion of the optical energy following its interaction with the workpiece. The present sensor also includes a signal processing system for determining temperature of the workpiece based on a measurement of an optical parameter affected by a temperature-dependent surface-roughness-induced light scattering phenomenon.

More particularly, the present invention comprises a non-invasive sensor for measuring semiconductor wafer temperature in real-time in semiconductor processing equipment. The present inventive sensor determines the wafer temperature based on changes in laser light scattering as a result of thermal expansion of the wafer. No special test structures are required on the wafer since the wafer backside surface roughness is used to enable the measurement. The sensor includes a first laser source to provide a first laser beam at a first wavelength, and a second laser source to provide a second laser beam at a second wavelength. (A single laser source employing wavelength modulation is also within the inventive concepts of the present invention.) The sensor includes wavelength modulating circuitry to modulate the wavelength of the first and second laser beams as the laser beams are directed to and reflected from the wafer surface. The sensor system also includes measuring circuitry to measure the change in reflectance of the wafer resulting from the modulation of the wavelengths of the first and second laser beams. The sensor also includes circuitry to determine surface roughness of the wafer at a known temperature from the change in specular reflectance of the wafer resulting from modulation of the wavelengths of the first and second laser beams. The circuitry also determines the temperature of the wafer from the change in specular reflectance of the wafer resulting from modulation of the wavelengths of the first and second laser beams.

A technical advantage of the present invention is that the temperature of the wafer can be determined non-invasively in real-time during the device fabrication process. Additionally, the sensor of the present invention can be integrated into existing semiconductor processing equipment, such as RTP equipment, providing a technical advantage of in-situ wafer temperature measurement. An additional technical advantage of the present invention is the wide range of temperatures it can measure, from cryogenic to high temperature (e.g., 200° C. to 1250° C.), with an accuracy and repeatability of better than ±2° C. Thus, the present inventive sensor can be used for various thermal and plasma fabrication processes. Moreover, the present sensor can be easily implemented for multi-point temperature measurements for measurement and control of wafer temperature uniformity.

Yet another technical advantage of the present sensor for measuring wafer temperature, is that it is not affected by changes in the surface emissivity of the wafer. Therefore it does not suffer the problems noted for pyrometry based systems. Also, the present temperature sensor is not affected by the RF or electromagnetic fields which may be present during semiconductor wafer processing. The sensor of the present invention is non-invasive, and therefore, provides a technical advantage of not interfering with processing of the semiconductor wafer. The sensor of the present invention is compatible with and effective in measuring temperature during such semiconductor processes as; etch, deposition, and anneal. Moreover, the present sensor is not disturbed by the heating lamp during RTP.

The sensor of the present invention provides an additional technical advantage of providing either single point or multi-point temperature measurements on a semiconductor wafer. Multi-point temperature measurements across a semiconductor wafer can be used to measure the temperature uniformity for the wafer which may be important in the fabrication process. Another technical advantage of the present invention is its low cost when compared to available temperature sensors. By using readily available lasers, the cost of the present temperature sensor is relatively low.

The sensor of the present invention can also be used in other applications not related to semiconductor wafer processing, and provides a technical advantage of being suitable for measuring the temperature of an object whenever non-invasive, in-situ, real-time, repeatable, and accurate measurements are desired.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Embodiments of the present invention and its advantages are best understood by referring to the Figures, like numerals being used for like and corresponding parts of the various drawings.

The present invention is based on the thermal expansion effects on the backside surface roughness-induced scattering of an incident laser beam. Standard silicon wafers, have unpolished backside surfaces with rms surface roughness values on the order of a few thousand angstroms, e.g., 5000Å. Any variation of wafer temperature has a corresponding thermal expansion effect in the wafer which changes the rms wafer backside surface roughness. The change in surface roughness r due to change in temperature can be represented by Equation 1.

$$\frac{1}{r} \frac{dr}{dT} = \alpha \quad (1)$$

where:

$\alpha$ is the coefficient of thermal expansion; and

T is the wafer temperature.

The linear thermal expansion coefficients $\alpha$ of silicon (Si) and germanium (Ge) are approximately $4.2 \times 10^{-6} °C.^{-1}$ and $6.1 \times 10^{-6} °C.^{-1}$ respectively Therefore, the change in surface roughness r due to the change in temperature T for silicon can be approximately represented by Equation 2.

$$\frac{1}{r} \frac{dr}{dT} \cong 4.2 \times 10^{-6}/°C. \quad (2)$$

Any change in backside surface roughness r in a wafer results in a change of the specular reflectance of the wafer. In practice, the thermal expansion coefficient $\alpha$ is somewhat temperature dependent. This temperature dependent parameter is a fundamental material characteristic and can be accurately tabulated over a wide range of temperatures as is known in the art.

Figure 1:
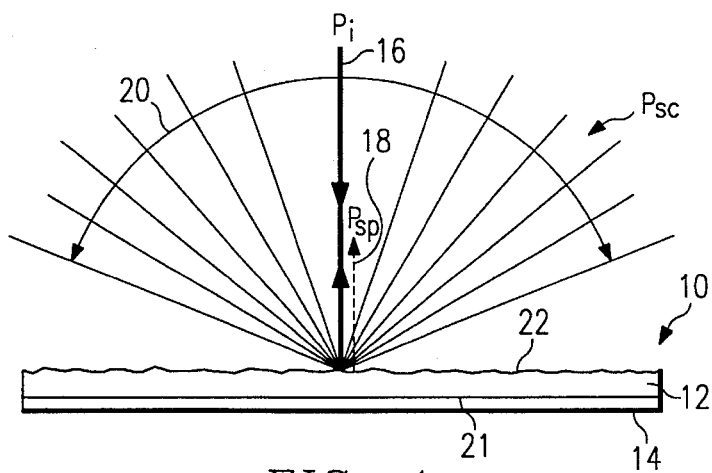
FIG. 1 is a schematic diagram illustrating the specular and scattered components of the reflected beam on the unpolished backside of a semiconductor wafer.

FIG. 1 depicts semiconductor wafer 10, with substrate 12 and device structure 14 fabricated on substrate 12. Also shown is coherent laser beam 16 of power $P_i$ directed to the backside surface of wafer 10. A portion of the incident laser beam is specular reflected as specular beam 18 (offset for illustration only) of power $P_{sp}$. The remaining portion of incident beam 16 is reflected and scattered from the semiconductor wafer surface over a span 20 with a scattered reflected power $P_{sc}$. Surface scattering parameter $S_r$ can be represented by Equation 3.

$$S_r = \frac{\text{scattered laser power}}{\text{(scattered + specular)laser power}} = \frac{P_{sc}}{P_{sc} + P_{sp}} \quad (3)$$

Typically, wafer 10 of FIG. 1 has a polished front surface 21 between substrate 12 and device structure 14, and an unpolished backside surface 22 on substrate 12. Polished surface 21 usually has a higher reflectivity than unpolished surface 22. The relationship between scattering parameter $S_r$ and the reflectance of the polished and unpolished surfaces may be represented by Equation 4.

$$1 - S_r = R/R_o \quad (4)$$

where:

$R_o$ is the surface specular reflectance for a polished surface; and

R is the surface specular reflectance for an unpolished or rough surface.

The relationship between the specular surface reflectance for the unpolished surface R to the polished surface specular reflectance $R_o$ may be represented approximately by Equation 5.

$$R = R_o e^{-(4\pi n_o)^2 (\frac{r}{\lambda})^2} \quad (5)$$

where:

r is the rms surface roughness;

$n_o$ is the refractive index of the medium the beam is traveling in; and $\lambda$ is the various wavelengths of the laser beam.

For a vacuum or air, $n_o=1$, then Equation 5 gives Equation 6 representing the relationship between the surface specular reflectance for polished and unpolished surfaces, $R_o$ and R, respectively, as a function of the rms surface roughness r.

$$R = R_o e^{-(\frac{4\pi r}{\lambda})^2} \quad (6)$$

Figure 2:
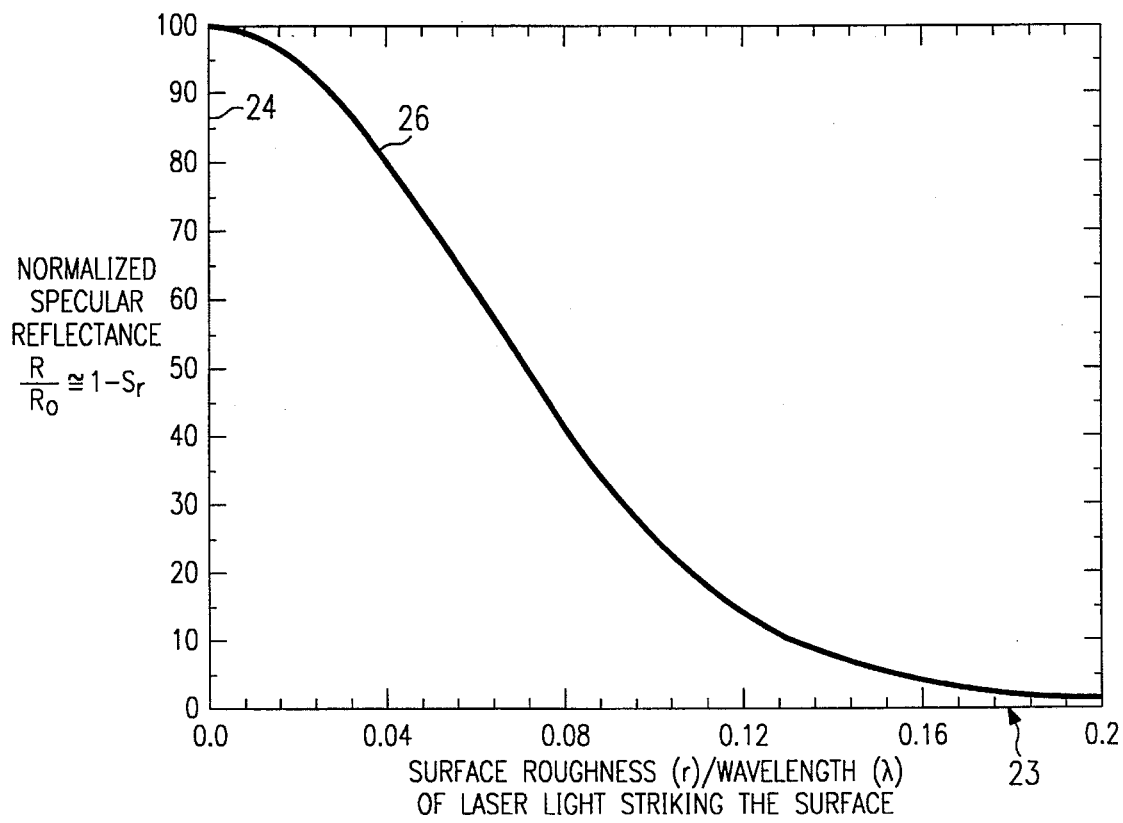
FIG. 2 depicts the typical relationship between the surface roughness and normalized specular reflectance of a wafer.

FIG. 2 shows a graphical representation of the relationship of Equation 6, where X-axis 23 is the rms surface roughness r of the wafer normalized to the wavelength $\lambda$ of the laser beam directed to wafer 10. Y-axis 24 is the specular reflectance R of the unpolished surface divided by specular reflectance $R_o$ of the polished surface, which according to Equation 4 above, provides the scattering parameter $S_r$. Line 26 shows the normalized specular reflectance decreases rapidly with increasing the normalized surface roughness r. Similarly, the scattering parameter Sr increases with larger surface roughness values. This corresponds (in FIG. 1) to an increase in the portion of the power from incident laser beam $P_i$ 16 that is scatter reflected in $P_{sc}$ 20 versus that which is reflected in $P_{sp}$ 18. Therefore, as the temperature T of wafer 10 changes, thermal expansion or contraction in wafer 10 causes the rms surface roughness r to change. A change in rms surface roughness r in turn, results in a change in normalized specular reflectance.

Using Equations 1 and 2, the change in specular reflectance R due to a change in temperature T can be represented by Equation 7.

$$\frac{1}{R} \frac{dR}{dT} = -2\alpha \left( \frac{4\pi r}{\lambda} \right)^2 \quad (7)$$

To determine the change in specular reflectance R due to a change in the wavelength $\lambda$ due to wavelength modulation of a laser beam directed at wafer 10, assume the change in polished surface reflectance $R_o$ for the wafer due to a change in wavelength $\lambda$ is a known value. Applying this assumption to Equations 6 and 7, and solving for the change in specular reflectance R due to a change in laser beam wavelength $\lambda$, gives Equation 8.

$$\frac{1}{R} \frac{dR}{d\lambda} = \frac{1}{R_o} \left( \frac{dR_o}{d\lambda} \right) + \frac{2}{\lambda^3} (4\pi r)^2 \quad (8)$$

Therefore, the change in surface specular reflectance R due to a change in wavelength $\lambda$ caused by wavelength modulation can be calculated.

If two laser beams with different wavelengths are used, then accurate temperature measurements without emissivity is achievable. Preferably, the choice of laser wavelengths must be so that the photon energies of both lasers are above the silicon bandgap energy of the wafer being tested making the wafer opaque to the laser wavelengths. Also, since silicon bandgap energy is reduced with increasing temperature T, the choice of wavelengths should be based on the smallest silicon bandgap energy, which is at the highest temperature the wafer experiences. Also, the wavelengths of the two laser beams are chosen to be close or adjacent to each other such that the relationship between the change in the polished surface specular reflectance $R_o$ due to a change in laser beam wavelength $\lambda$ at the two close wavelengths can be represented by Equation 9.

$$\frac{1}{R_o} \left( \frac{dR_o}{d\lambda} \right) \bigg|_{\lambda=\lambda_1} \cong \frac{1}{R_o} \left( \frac{dR_o}{d\lambda} \right) \bigg|_{\lambda=\lambda_2} \quad (9)$$

This implies that the normalized variations of the specular reflectance values with laser wavelength variations are equal at two adjacent center wavelengths $\lambda_1$ and $\lambda_2$.

One possible choice for laser beam 1 and laser beam 2 to meet the requirements of Equation 9 are laser beam at a wavelength of 850 nanometers (nm) and laser beam 2 at a wavelength of 820 nm. Single mode diode lasers which can be tuned by modulating the laser current meet this requirement. Another possible choice is laser beam 1 at a wavelength of 820 nm and laser beam 2 at a wavelength of 780 nm. Both of these lasers are also diode lasers which are commercially available, at relatively low costs.

Therefore, a change in unpolished surface specular reflectance R of wafer 10 due to a change in wavelength $\lambda$ in both laser beam 1 and laser beam 2 can be represented by Equation 10.

$$\left[ \frac{1}{R} \left( \frac{dR}{d\lambda} \right) \right]_{\lambda=\lambda_1} - \left[ \frac{1}{R} \left( \frac{dR}{d\lambda} \right) \right]_{\lambda=\lambda_2} = 2(4\pi r)^2 \left[ \frac{1}{\lambda_1^3} - \frac{1}{\lambda_2^3} \right] \quad (10)$$

for $\lambda_1 > \lambda_2$, resulting in Equation 11.

$$\left[ \frac{1}{R} \frac{dR}{d\lambda} \right]_{\lambda=\lambda_1} - \left[ \frac{1}{R} \left( \frac{dR}{d\lambda} \right) \right]_{\lambda=\lambda_2} = \frac{(4\sqrt{2} \pi r)^2}{\lambda_2^3} \left[ 1 - \left( \frac{\lambda_2}{\lambda_1} \right)^3 \right] \quad (11)$$

Knowing that the change in specular reflectance R due to a change in temperature T can be represented by Equation 7, and the change in rms surface roughness r of the wafer surface due to a change in temperature T can be represented by Equation 1, and assuming:

$$r = r_o[1 + \alpha(T - T_o)] \quad (12)$$

where $r_o$ is the rms surface roughness of unpolished backside surface of wafer 10 at room temperature or another known temperature; and r is the rms surface roughness of unpolished backside surface of wafer 10 at the temperature being measured Then substituting Equation 12 into Equation 11 gives Equation 13, for which the unknown temperature T can be solved.

$$\left[ \frac{1}{R} \left( \frac{dR}{d\lambda} \right) \right]_{\lambda=\lambda_1} - \left[ \frac{1}{R} \left( \frac{dR}{d\lambda} \right) \right]_{\lambda=\lambda_2} = \frac{(4\sqrt{2}\,\pi r_o)^2}{\lambda_2^3} \left[ 1 - \left( \frac{\lambda_2}{\lambda_1} \right)^3 \right] [1+\alpha(T-300)]^2 \quad (13)$$

Therefore, the temperature of wafer 10 can be determined by obtaining the rms surface roughness $r_o$ at a known temperature (such as room temperature) by measuring a change in specular reflectance R due to a change in wavelength $\lambda$ for the first and second laser beams and applying Equation 11. The known temperature is generally room temperature (300° K.). To determine an unknown temperature, a change in reflectance R due to a change in wavelength $\lambda$ for the first and second laser beams is measured at the unknown temperature, and using those measurements and applying Equation 13, the temperature T of wafer 10 can be determined.

The resolution of the temperature sensor of the present invention is quite acceptable for device processing applications. For example, it is known that:

$r_o = r$ at $T=T_o=300°$ K. (room T),
Assume:
l=850 nm, and
r=5000Å or 500 nm, and
$\alpha=4.2\times10^{-6}$ $C^{-1}$ for Silicon
Then, applying Equation 7 gives $$\left[ \frac{1}{R} \frac{dR}{dT} \right]_{\lambda=\lambda_1} = -2(4.2\times10^{-6})\left( \frac{4\pi \times 500\,\text{nm}}{850\,\text{nm}} \right)^2 /°C.$$

giving, $$\left[ \frac{1}{r} \frac{dR}{dT} \right]_{\lambda=\lambda_1} = -4.59\times10^{-4}/°C.,$$

or $$\left[ \frac{1}{r} \frac{dR}{dT} \right]_{\lambda=\lambda_1} = -459\,\text{ppm}/°C.$$

This gives a temperature measurement resolution of less than one degree Celsius. This also implies that shorter laser wavelengths enhance measurement sensitivity, and for laser wavelength $\lambda$ of 850 nm, a 1° C. change in wafer temperature results in a 460 ppm change in reflected power $P_{sp}$ from the wafer surface. This specular reflectance sensitivity will provide temperature measurement sensitivities within 1° C.

Figure 3:
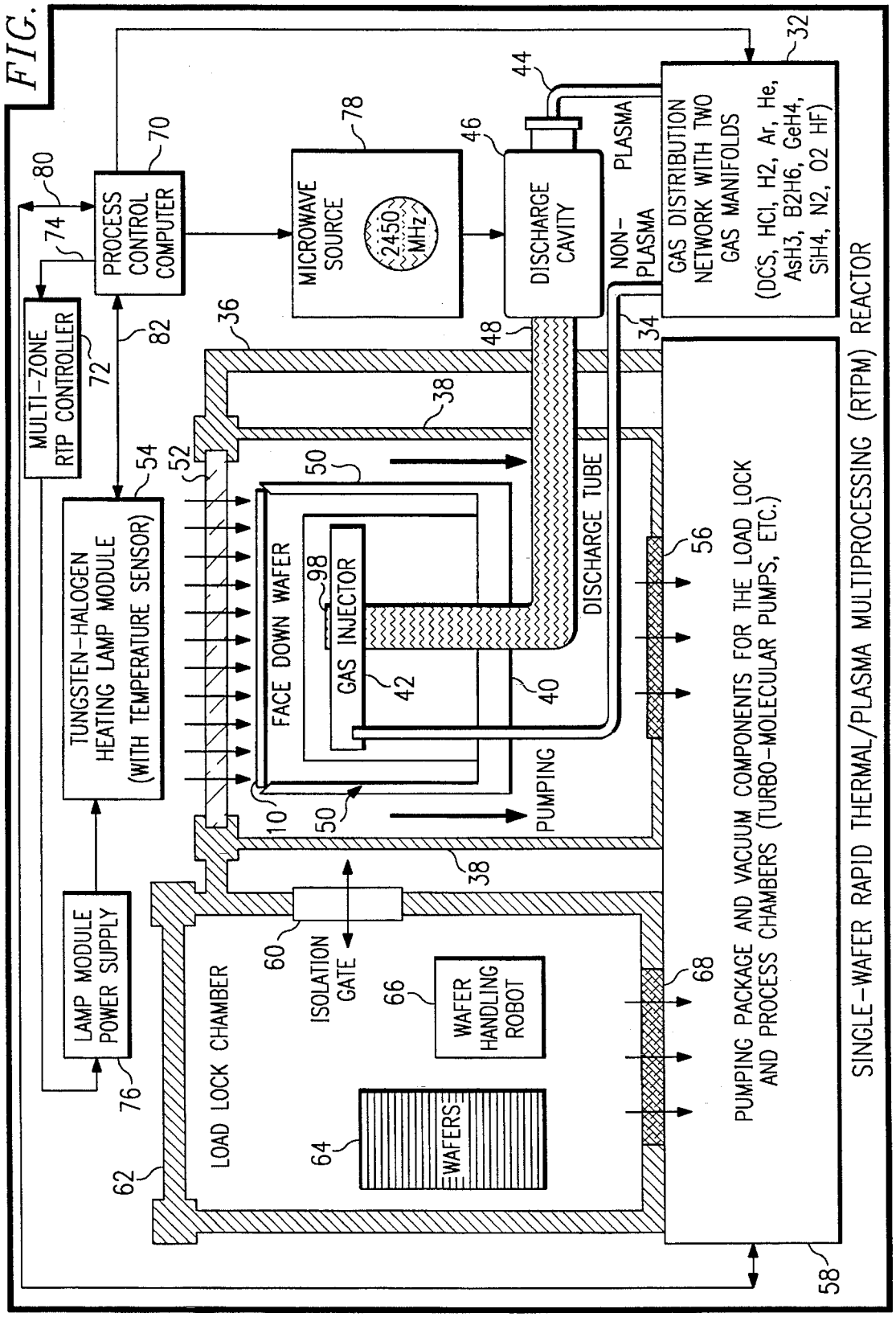
FIG. 3 is a schematic drawing of a single-wafer semiconductor device fabrication reactor using the temperature sensor of the present invention.

FIG. 3 depicts a schematic representation of a semiconductor fabrication reactor 30 establishing a representative single-wafer environment of the present invention. Within a single-wafer rapid thermal/plasma processing reactor such as the Texas Instruments' Automated Vacuum Processor (AVP), may reside semiconductor wafer 10 for device processing. Beginning at the bottom right-hand corner of FIG. 3, gas distribution network 32 may comprise two gas manifolds: a non-plasma process gas manifold (not shown) and a plasma manifold. Non-plasma process gas manifold connects to gas line 34 which penetrates through reactor casing 36 and process chamber wall 38 to proceed through ground electrode 40 and into gas injector 42. Plasma manifold connects via gas line 44 into discharge cavity 46 for generating process plasma. Process plasma activated species pass within plasma discharge tube 48 through reactor casing 36 and process chamber wall 38, through ground electrode 40, and into the wafer process environment.

Above gas injector assembly 42, and supported by low thermal mass pins 50, appears semiconductor wafer 10. Low thermal mass pins 50 are supported by ground electrode 40 within process chamber 38. Process chamber 38 includes optical quartz window 52 which separates semiconductor wafer 10 from tungsten-halogen heating lamp module 54. In one embodiment of the present sensor, tungsten halogen heating lamp module 54 includes one or more temperature sensors of the present invention which subsequent Figures and associated text describe.

Process chamber 38 also includes pump down interface 56 which removes process gas and plasma into pumping package 58. Additionally, isolation gate 60 permits passage of semiconductor wafers from the load-lock chamber 62 into process chamber 38. To permit movement of semiconductor wafers into process chamber 38, process chamber wall 38 is supported by a vertically moving element (not shown). Within load-lock chamber 62 appears a cassette of semiconductor wafers 64 from which wafer handling robot 66 removes a single semiconductor wafer 10 for processing. To maintain load-lock chamber 62 and process chamber 38 under vacuum, load-lock chamber 62 also includes vacuum pump interface 68 which permits pumping package 58 to maintain a vacuum.

Process control computer 70 controls the fabrication of semiconductor wafer 10 in reactor 38 of FIG. 3. Control signals from process control computer 70 include signals to multi-zone temperature/lamp power control 72 on line 74. Multi-zone controller 72 provides various control signals to lamp module power supply 76. Lamp module power supply 76, in turn, provides various control signals to tungsten-halogen heating lamp module 54. Process control computer 70 also directs control vacuum setpoints to pumping package 58 and gas and plasma inlet flow signals to gas distribution network 32. To provide proper activation of plasma species at discharge cavity 46, process control computer 70 provides a control signal to microwave source 78 which, in one embodiment, operates at a frequency of 2450 MHz.

To control the input power levels to tungsten-halogen heating lamp module 54, process control computer 70 sends power control signals via line 74 to multi-zone controller 72 in response to the temperature sensor outputs (received via sensing lines 82). Sensing lines 82 to process control computer 70 from tungsten-halogen heating lamp module 54 include signals from the temperature sensor of the present invention which measures the temperature of semiconductor wafer 10 in real-time at multiple points on the wafer.

Figure 4:
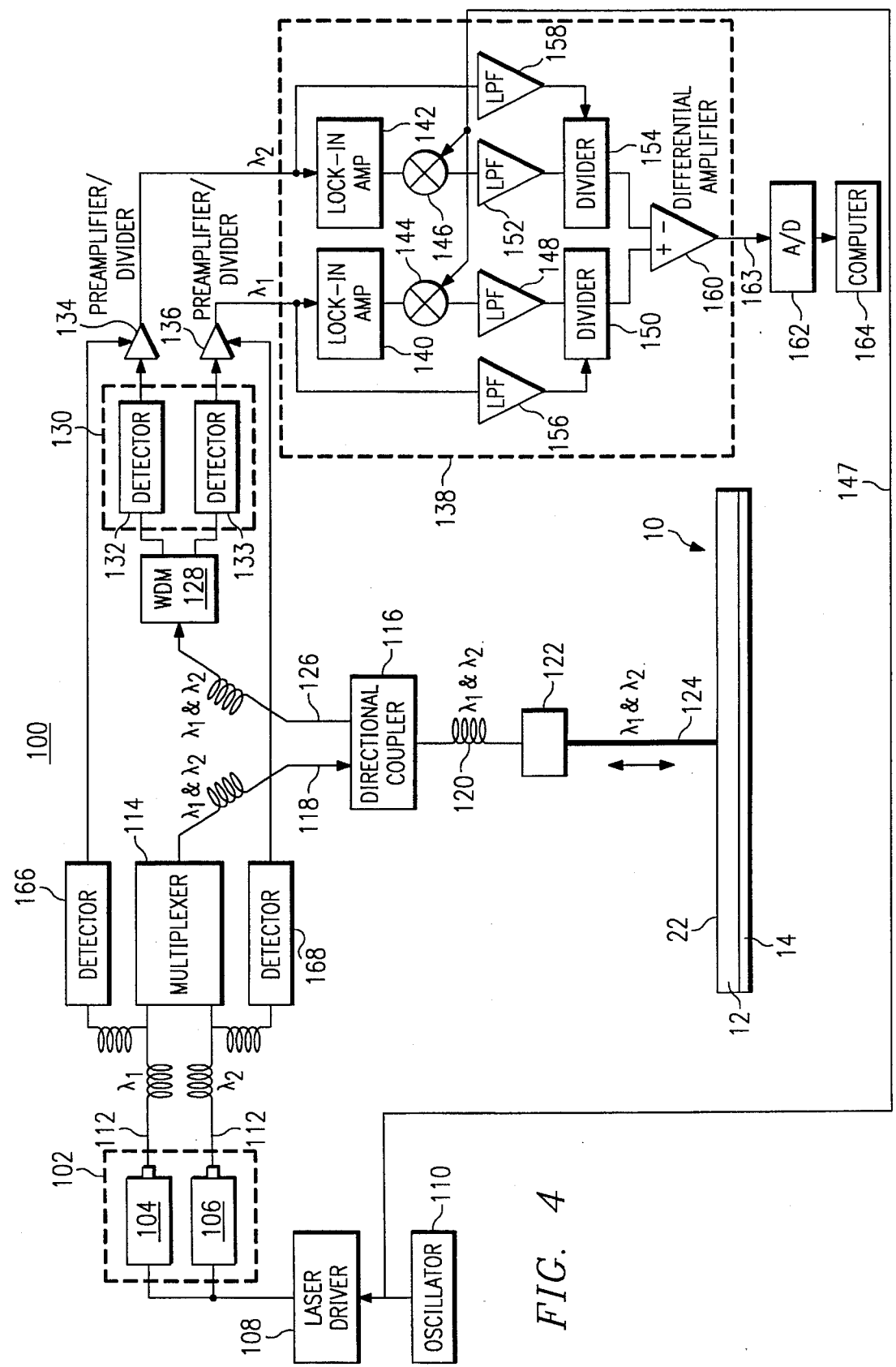
FIG. 4 is a schematic drawing illustrating a preferred embodiment of the present invention.

FIG. 4 depicts a schematic diagram of temperature sensor 100 which is an embodiment of the present invention. Sensor 100 includes an optical energy source or laser source 102 which includes first laser 104 and second laser 106. Laser source 102 receives power from laser driver 108, which in turn receives modulation signals from oscillator 110. Oscillator 110 could in turn be controlled by process control computer 70 of FIG. 3.

In one embodiment of sensor 100, the wavelengths of laser 104 and laser 106 have been selected to be 850 nm and 820 nm, respectively, for silicon wafer temperature measurements. Other combinations of laser 104 at a wavelength λ of 820 nm and laser 106 at a wavelength λ of 810 nm, or laser 104 at a wavelength λ of 810 nm and laser 106 at 780 nm can also be used for silicon wafer temperature measurements. Laser source 102 is coupled by a pair of optical fibers 112 to multiplexer 114. Multiplexer 114 combines the laser beams it receives into a single composite beam and is coupled to directional coupler 116 by fiber-optic cable 118. In an alternate embodiment, multiplexer 114 is an optical fiber bundle. Directional coupler 116 is coupled through fiber-optic cable 120 to fiber termination and collimating lens 122. It is noted that directional coupler 116 can be replaced with a fiber bundle without departing from the inventive concepts of the present invention.

Lens 122 directs laser beam 124, which is a combined laser beam from first laser 104 and second laser 106, to and from wafer 10. Wafer 10 is positioned in apparatus 100 such that the rough backside surface 22 of wafer 10 is facing lens 122, and the frontside surface of wafer 10, which may simultaneously be under a fabrication process, is facing away from lens 122.

Directional coupler 116 is coupled by fiber-optic cable 126 to wavelength division demultiplexer (WDM) 128. WDM 128 is coupled to detector module 130. Detector module 130 comprises first detector 132 and second detector 133 which may be low noise sensitive detectors. Germanium, silicon, or avalanche photodetectors also can be successfully used in detector module 130. First detector 132 is coupled to first pre-amplifier/divider 134, and second detector 133 is coupled to second preamplifier/divider 136. The outputs of preamplifiers/dividers 134 and 136 are fed to signal processor 138.

Signal processor 138 may have many analog, digital, or hybrid embodiments, and it is not intended that signal processor 138 be limited to the design shown in FIG. 4. In fact, signal processor 138 may be designed to include laser driver 108, oscillator 110, detector module 130, preamplifiers/dividers 134 and 136, and detectors 166 and 168. Signal processor 138 includes lock-in amplifier 140 coupled to second pre-amplifier/divider 136, and lock-in amplifier 142 that is coupled to first preamplifier/divider 134. Signal processor 138 also includes first mixer 144 coupled to lock-in amplifier 140, and second mixer 146 coupled to lock-in amplifier 142. These mixers multiply the outputs of their respective lock-in amplifiers by a fraction of the laser modulation oscillator signal from oscillator 110 supplied on line 147.

Signal processor 138 also includes low-pass filters, including low-pass filter 148 coupled to first mixer 144 and to first divider 150. Low-pass filter 152 is coupled to second mixer 146 and second divider 154. Low-pass filter 156 is coupled between pre-amplifier/divider 136 and first divider 150, and low-pass filter 158 is coupled between first pre-amplifier/divider 134 and second divider 154. The outputs of dividers 150 and 154 are coupled to differential amplifier 160 which provides the output of signal processor 138.

The output of signal processor 138 is coupled to analog to digital converter 162, which is in turn coupled to computer 164. In an alternate embodiment computer 164 may be embodied in process control computer 70 of FIG. 3.

Output signal 163 of signal processor 138 corresponds to:

$$\left[\frac{1}{R}\left(\frac{dR}{d\lambda}\right)\right]_{\lambda=\lambda_1} - \left[\frac{1}{R}\left(\frac{dR}{d\lambda}\right)\right]_{\lambda=\lambda_2}$$

of Equations 10 and 13. Computer 164 extracts the temperature of wafer 10 based on measurements at a reference (e.g., room) temperature and at any unknown temperature.

Figure 5:
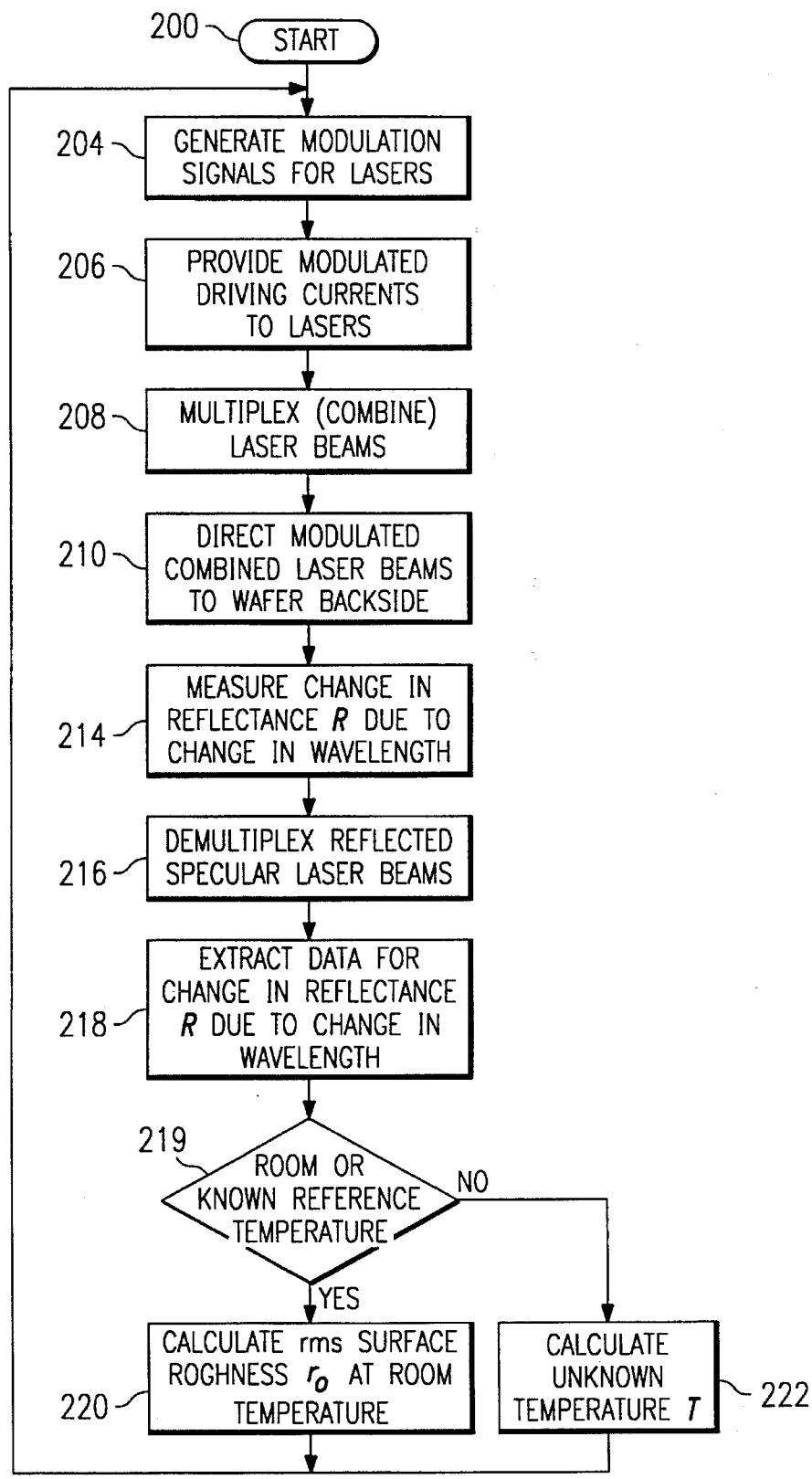
FIG. 5 is a flow chart showing the methodology executed by the temperature sensor of the present invention.

FIG. 5 is representative of functional steps executed by sensor 100 of FIG. 4 of the present invention in real-time non-contact measurements of the temperature of wafer 10. The process is started at step 200 while the temperature of wafer 10 is known, typically at a known reference temperature such as room temperature (300° K.). To first measure the rms surface roughness $r_o$ of wafer 10, at step 204 oscillator 110 provides the modulation signals for laser driver 108 to laser source 102. At step 206, laser driver 108 provides modulated electrical currents to laser source 102. Within laser source 102, first laser 104 and second laser 106 provide by way of fiber-optic cables 112 first and second laser beams to multiplexer or combiner 114. At step 208, multiplexer 114 combines the two laser beams into a single beam. In step 210, the combined laser beams are directed to and from wafer 10. This is accomplished by multiplexer 114 providing combined beam 124 on fiber-optic cable 118 to directional coupler 116. Directional coupler 116 or fiber bundle controls the direction of signals traveling on fiber-optic cable 120 between directional coupler 116 and collimating/collecting lens 122. Directional coupler 116 allows the laser beams from multiplexer 114 to travel on fiber-optic cable 120 to lens 122. Lens 122 projects by collimation or focusing multiplexed first and second laser beams 124 to backside surface 22 of wafer 10 and also receives the specular reflected beam.

In order to calculate the backside roughness $r_o$ at the known reference temperature or room temperature with Equation 11, it is necessary to measure the change in specular reflectance R of wafer 10 backside surface 22 due to a change in wavelength λ around the center wavelengths of two laser beams directed to wafer 10. This is accomplished by modulating the wavelengths λ of the two laser beams in composite beam 124 at step 206. The change in specular reflectance values are determined by measuring the change in specular reflected power $P_{sp}$ values when the laser wavelengths of beam 124 are modulated at step 206 and separated at step 216. The reflected specular power $P_{sp}$ values provide the scattering parameter values, which in turn, can be used to calculate the backside surface roughness of wafer 10 at room temperature.

The reflected specular power laser beam 124 is collated by lens 122 and transferred by fiber-optic cable 120 to directional coupler 116. On the return path, directional coupler 116 (or fiber bundle) directs the reflected specular laser beam via fiber-optic cable 126 to WDM 128. At step 216, WDM 128 demultiplexes composite beam 124 into reflected specular beams consisting of a specular first laser beam and a specular second laser beam, and provides signals representative of the demultiplexed or separated beams to detector module 130.

At step 218 the extraction of the necessary data to determine the rms surface roughness $r_o$ begins. In detector module 130, first detector 132 and second detector 133 measure the power of the reflected laser beams for processing within signal processor 138. Preamplifiers/dividers 134 and 136 condition the signals from detectors 132 and 133, respectively, for processing within signal processor 138.

In step 218, signal processor 138 extracts the necessary information from the signals representative of the specular reflected beams so that the change in reflectance R due to a change in wavelength λ of the beams can be identified. At step 219 a query is made as to whether the temperature T of wafer 10 is known. Assuming that the wafer is at a known temperature such as room temperature, the flow proceeds to step 220. In step 220, applying Equation 11, computer 164 can calculate the rms surface roughness $r_o$ of backside surface 22 of wafer 10. Once the rms surface roughness $r_o$ is determined the flow returns to step 204 for continuous real-time wafer temperature measurements.

To determine the unknown temperature of wafer 10 at a later time, the process steps described for FIG. 5 are repeated with the exception that at step 219, where the temperature T of water 10 is unknown, the flow proceeds to step 222. The changes in reflectance R due to wavelength λ modulation of the lasers are measured by executing steps 204 through 218 of FIG. 5, and by knowing the value of the rms surface roughness $r_o$ at room temperature, the unknown temperature T can be obtained in real-time with Equation 13 at step 222.

For enhanced signal-to-noise performance in sensor 100 of FIG. 4, cooling detector module 130 has been found to be effective. For example, using thermoelectric cooling, and operating detector module at temperatures below room temperature reduces noise problems in sensor 100. Also, the wavelengths from laser source 102 can be optimized by cooling laser source 102. This provides enhanced signal-to-noise ratio and temperature measurement accuracy in sensor 100.

When measuring the changes in specular reflectance due to the changes in wavelengths, modulation of the laser beams is employed. This can be accomplished by using a square wave or a triangular wave from oscillator 110 to laser driver 108. Additional detectors 166 and 168 as shown in FIG. 4 can be used to measure the incident laser beam power levels. Detectors 166 and 168 provide signals that are proportional to the incident beam power levels. By dividing the outputs of detectors 132 and 133 by the outputs of detectors 166 and 168, respectively, the effects of laser power drifts and noise can be cancelled out. The results of the division are fed to signal processor 138 via preamplifiers/dividers 134 and 136. This allows for significant enhancement of the signal-to-noise ratio and measurement repeatability of system 100.

Laser current and wavelength modulations can also be accomplished by using sinusoidal signals from oscillator 110 instead of triangular or square wave modulations. Laser source 102 can be kept at a constant temperature to eliminate any temperature related drifts. Moreover, if all four detectors 132, 133, 166, and 168 are cooled to a temperature between 200° K. and 300° K., this minimizes low noise effects and maximizes measurement resolution and repeatability. It is also possible to use interferometry to determine the precise change in wavelength λ in each laser beam due to modulation.

Figure 6:
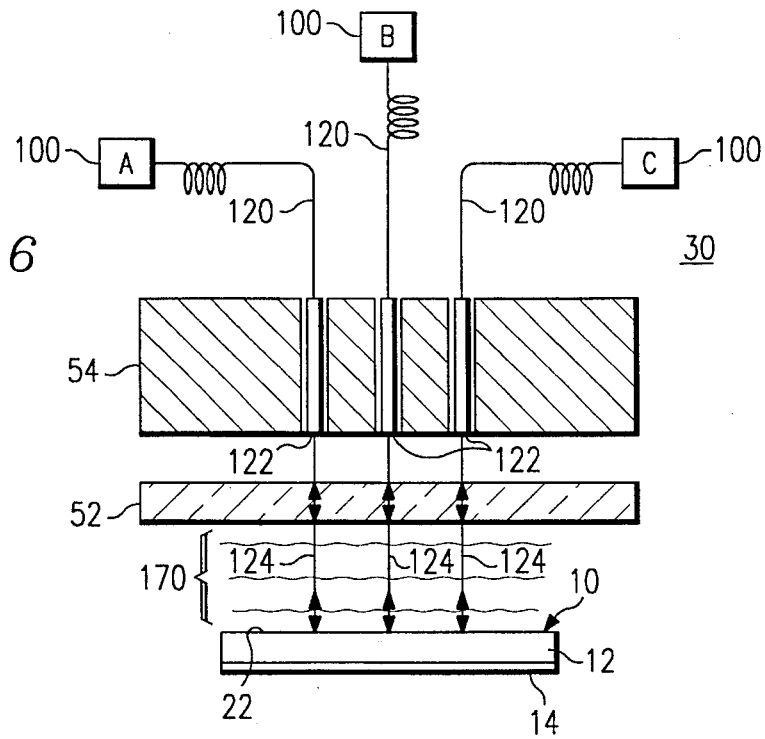
FIG. 6 is a schematic drawing illustrating a preferred embodiment of the present invention.

FIG. 6 is a schematic drawing illustrating a preferred embodiment of the temperature sensor of the present invention showing the sensor's integration into the rapid thermal processing chamber 30 of FIG. 3. In this figure, semiconductor wafer 10 is placed face down with backside 22 facing the temperature sensors. FIG. 6 includes three wafer temperature sensors 100 arranged to provide multipoint temperature measurements on wafer 10. There is no limitation on the number of sensor probes used for temperature profile measurements on a wafer. Fiber termination and collimating lens 122 of each temperature sensor 100 is shown secured in hollow light pipes located within heating lamp module 54. FIG. 6 shows wafer 10 positioned below optical quartz window 52. Optical window 52 not only serves to transfer lamp optical flux and sensor laser beams to wafer 10, but also maintains a controlled process environment within the process chamber for processing semiconductor wafer 10. Optical window 52 is optically transparent for both lamp energy from lamp module 54 and the incident coherent laser beams 124 transmitted and received by each temperature sensor 100. Optical transparency is a function of the window material and the wavelength of the optical energy passing through optical window 52, so the material for window 52 is selected with optical transparency in the desired band as an essential feature. For, example, for 1.3 um laser beams, a window material such as quartz can be used. Wavelengths larger than 4 nm will require alternative window materials, such as sapphire.

The operation of the multipoint temperature sensors of FIG. 6 is as described for the operation of temperature sensor 100 of FIG. 4. Each temperature sensor 100 causes laser beam 124 to be transmitted by lens 122 through quartz window 52 and through wafer backside ambient 170. Each laser beam 124 strikes wafer 10 backside and a portion of the reflected beam is transmitted as a specular beam back to lens 122, and the remaining portion is scatter reflected. To measure the change in specular reflectance of wafer 10 backside due to laser wavelength modulation, each laser beam is modulated and its effects are measured. Using the measured change in specular reflectance values, and measured room-temperature rms surface roughness $r_o$ for wafer 10, the temperature of wafer 10 is calculated in real-time for the wafer positions corresponding to the sensor probe locations.

It is noted that by including multiple temperature sensors 100 within RTP reactor 30, it is possible to measure a temperature map or profile for wafer 10. The measured temperature values by each system 100 can be fed into a multi-zone temperature control system for establishing uniform and repeatable processing. It should also be noted that each lens 122 of the temperature sensors shown in FIG. 5 can be coupled to a fiber bundle. A fiber bundle can be used to transmit the laser beam (with two multiplexed wavelengths) and to receive a specular reflected beam in each sensor probe.

Figure 7:
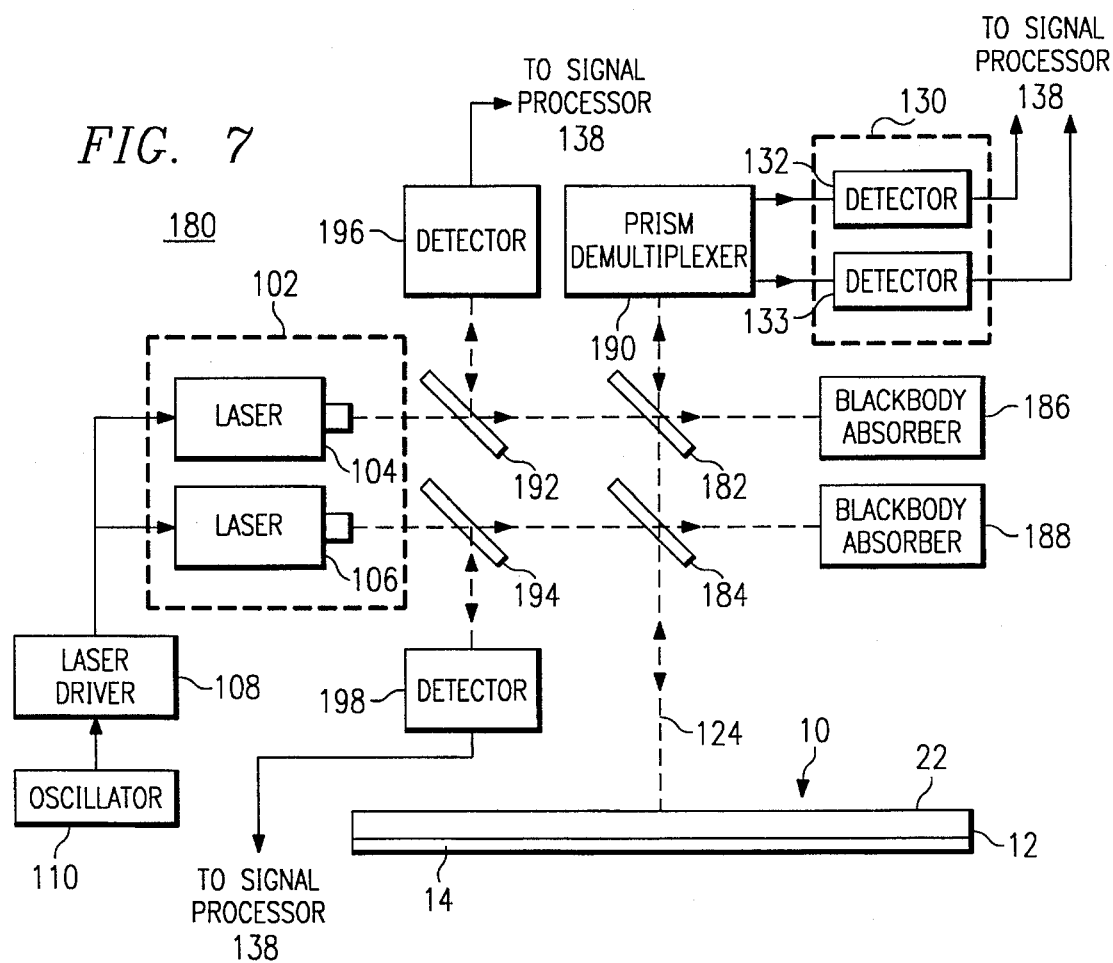
FIG. 7 depicts a schematic diagram of another embodiment of the present invention utilizing beam splitters and mirrors.

FIG. 7 shows an alternate embodiment of the present invention based on the use of mirrors and splitters instead of fibers. In addition to those similar components of temperature sensor 100 of FIG. 4, the wafer temperature measuring sensor 180 of FIG. 7 includes beam splitters 182, 184, 192, and 194. First laser 104 directs a first beam at splitter 192 which splits the first laser beam directing a portion onto detector 196 and the remainder of first laser beam to beam splitter 182. Beam splitter 182 then sends a fraction of the beam to beam splitter 184 which in turn sends a fraction of the beam originated from first laser 104 to wafer 10. Second laser 106 directs a second laser beam to splitter 194 which splits second laser beam into two portions. The first portion travels to detector 198 and the remainder to beam splitter 184. Beam splitter 184 combines a fraction of the laser beam from laser source 106 with a fraction of the beam from first laser source 104 and sends the combined beam to wafer backside 22.

The combined portions of laser 104 and 106 beams form combined beam 124 which is directed towards wafer 10 and its specular reflected portion is guided by beam splitters 182 and 184 towards prism demultiplexer 190. Prism demultiplexer 190 performs wavelength division demultiplexing on the specular reflected combined laser beams and provides the separated reflected first and second beams to detector module 130. The output signals of detector module 130 are provided to signal processor 138 (not explicitly shown in FIG. 3) for processing as described in connection with the discussions for FIG. 4.

The lasers of laser source 102 depicted in FIG. 7 can be tunable diode lasers. Tunable diode lasers can be modulated by modulating their drive current with laser driver 108 and oscillator 110. Current modulation varies the laser output wavelengths and the intensities of the laser beams from laser source 102, resulting in simultaneous amplitude and frequency modulation. In an ideal system only modulation of the laser wavelengths by modulating their intensity levels would occur. However, this may not be possible. Therefore, beam splitters 192 and 194, and detectors 196 and 198 are used to monitor the intensities of the incident laser beams from lasers 104 and 106. The output signals from detectors 132 and 133 are then divided by the output signals from detectors 196 and 198, respectively, in order to cancel intensity variation effects.

Black body absorbers 186 and 188 dissipate the excess laser beam powers exiting beam splitters 182 and 184 in the directions of the original incident beams.

In either embodiment of wafer temperature measuring apparatus shown in FIGS. 4 or 7, a single laser can be employed rather than the two shown. The single laser embodiment also has capability for direct measurement of the surface roughness and calculation of wafer temperature. The one laser apparatus must provide real-time measurement of both the specular as well as scattered reflected beams off of the wafer surface.

It is also noted, that while the several embodiments of the present invention have been discussed in connection with obtaining the rms surface roughness and specular reflectance from backside surface 22 of wafer 10, the present invention can also be used to measure temperature T of wafer 10 by directing the laser beams to the frontside surface of wafer 10. Measuring the change in specular reflectance due to the change in wavelength on the front side of wafer 10 can be accomplished with the sensor of the present invention. Also, the several embodiments of the present invention discussed herein can also be used in applications other than semiconductor processing. The sensor of the present invention is effective in measuring the temperature of any workpiece.

Although the present invention has been described in detail, it should be understood that various changes, substitutions, and alterations can be made hereto without departing from the spirit and scope of the invention as described by the appended claims.

What is claimed is:

1. A method for measuring the temperature of a semiconductor wafer, comprising the steps of:

generating a first laser beam at a first wavelength;

generating a second laser beam at a second wavelength;

simultaneously reflecting the first and second laser beams off the wafer while said wafer is at a reference temperature;

modulating the wavelengths of the first and second laser beams while said wafer is at said reference temperature;

measuring first and second rates of change in specular reflectance of the water as functions of wavelength corresponding to the first and second modulated laser beam wavelengths while the wafer is at said reference temperature;

determining a surface roughness characteristic of the wafer at the reference temperature by use of said first and second rates of change in specular reflectance at said reference temperature;

simultaneously reflecting the first and second laser beams off the wafer while the wafer is at an unknown temperature;

simultaneously modulating the wavelengths of the first and second laser beams while said wafer is at said unknown temperature;

again measuring first and second rates of change in specular reflectance of the water as functions of wavelength corresponding to the first and second modulated laser beam wavelengths while the wafer is at the unknown temperature; and determining the unknown temperature from the measured surface roughness characteristic of the wafer at the reference temperature and the first and second rates of change in specular reflectance of the wafer at the unknown temperature.

2. The method of claim 1 further comprising the steps of:

combining the first and second laser beams into a combined beam before said reflecting steps; and separating the combined beam into the first and second laser beams before said measuring steps.

3. The method of claim 1 further comprising the steps of:

measuring the intensities of the first and second laser beams prior to said reflecting steps;

measuring the intensities of the first and second laser beams after said reflecting steps; and compensating for effects of power variations of the first and second laser beams using the measured intensities of the first and second laser beams prior to and after said reflecting steps.

4. The method of claim 1 further comprising the step of selecting the unmodulated wavelengths of the first and second laser beams such that the normalized derivatives of the specular reflectance parameter with respect to wavelength at the unmodulated first and second laser beam wavelengths are essentially equal.

* * * * *